US007381696B2

(12) United States Patent
Hubert et al.

(10) Patent No.: US 7,381,696 B2
(45) Date of Patent: *Jun. 3, 2008

(54) AQUEOUS FOAMABLE CONCENTRATES AND METHODS

(75) Inventors: Mitchell J. Hubert, Menominee, MI (US); Gregory R. Walker, Marinette, WI (US)

(73) Assignee: Ansul, Incorporated, Marinette, WI (US)

(*) Notice: Subject to any disclaimer, the term of this patent is extended or adjusted under 35 U.S.C. 154(b) by 267 days.

This patent is subject to a terminal disclaimer.

(21) Appl. No.: 10/074,814

(22) Filed: Feb. 13, 2002

(65) Prior Publication Data

US 2002/0072481 A1 Jun. 13, 2002

Related U.S. Application Data

(63) Continuation of application No. 09/627,889, filed on Jul. 28, 2000.

(51) Int. Cl.
*A61K 7/50* (2006.01)

(52) U.S. Cl. ...................... 510/473; 510/492; 510/506; 588/259; 252/3; 405/66; 169/46

(58) Field of Classification Search ................ 510/432, 510/417, 506, 424, 238; 521/921, 913, 907, 521/85, 84.1, 70, 69; 405/128, 263
See application file for complete search history.

(56) References Cited

U.S. PATENT DOCUMENTS 4,060,489 A 11/1977 Chiesa, Jr.
4,190,428 A 2/1980 Colton et al.
4,619,711 A 10/1986 Olbrueck et al.
4,795,590 A * 1/1989 Kent et al. .................. 588/249
4,795,764 A * 1/1989 Alm et al. .................. 521/107
4,889,654 A 12/1989 Mason et al.
4,923,903 A * 5/1990 Alm et al. .................... 521/65
4,938,936 A 7/1990 Yan
5,019,289 A * 5/1991 Gray et al.
5,026,735 A * 6/1991 Stern ........................... 521/50
5,096,616 A 3/1992 Kittle
5,124,363 A * 6/1992 Stern ........................... 521/50
5,133,991 A * 7/1992 Norman et al. ............. 427/136
5,225,095 A 7/1993 DiMaio et al.
5,232,632 A * 8/1993 Woo et al. .................. 510/406
5,406,019 A * 4/1995 Dean .......................... 588/249
5,434,192 A 7/1995 Thach et al.
5,462,390 A * 10/1995 Sydansk ..................... 405/264
5,509,969 A * 4/1996 Grawe ........................... 134/2
5,782,580 A * 7/1998 Aubert et al. .......... 405/128.75
5,997,758 A 12/1999 Barbarin et al.
6,015,838 A 1/2000 Stern et al.
6,021,926 A 2/2000 Lauwers et al.
6,245,728 B1 * 6/2001 Robbins et al.
6,262,128 B1 * 7/2001 Stern et al. .................... 516/10
6,599,872 B1 * 7/2003 Hubert et al. ............... 510/473
6,627,590 B1 * 9/2003 Sherry et al. ............... 510/238

FOREIGN PATENT DOCUMENTS

| | | |
|---|---|---|
| DE | 2 908 736 | 9/1979 |
| DE | 1 95 31 089 | 2/1997 |
| EP | 0 286 149 | 10/1988 |
| EP | 0 526 305 | 2/1993 |

OTHER PUBLICATIONS

A copy of the International Search Report relating to the corresponding PCT case No. PCT/US01/23302 (3pgs).

* cited by examiner

*Primary Examiner*—Gregory Webb
(74) *Attorney, Agent, or Firm*—The Small Patent Law Group

(57) ABSTRACT

Novel aqueous foamable concentrates are disclosed. When mixed with a non-neutral pH aqueous liquid and foamed, the resulting foam is suitable for blanketing and neutralizing non-neutral pH hazardous material spills.

26 Claims, No Drawings

AQUEOUS FOAMABLE CONCENTRATES AND METHODS

The present application is a continuation of co-pending U.S. patent application Ser. No. 09/627,889 filed on Jul. 28, 2000.

INTRODUCTION

The present invention relates to materials and methods for the treatment of hazardous waste spills, especially work place spills of liquid hazardous materials.

BACKGROUND

It is known to use a layer of foam as a temporary blanket or cover over hazardous material spills. Persistent foams are taught, for example, in U.S. Pat. No. 5,434,192 to suppress the release of hydrocarbon and polar organic vapors during loading of oil tankers, as well as during the transportation, transfer, storage and accidental storage and accidental spillage or crude oil and the like. Aqueous foamable compositions for fighting fires on hydrophobic or hydrophilic liquids are disclosed in U.S. Pat. No. 4,060,489. Each of the two foregoing U.S. patents is incorporated herein by reference in its entirety. Aqueous film-forming foam (AFFF) compositions and other fire fighting foam compositions (such as protein, fluoroprotein and synthetic detergents), referred to here in some cases as aqueous foamable concentrates, are known for these and other applications. Improved compositions are required, however, for treating liquid hazardous waste spills, especially spills of non-neutral pH liquid hazardous materials, that is, spills of acidic or caustic liquids, and especially workplace spills. The paper industry is under pressure to substitute chlorine dioxide for aqueous solution chlorine in paper production processes. Chlorine dioxide is slightly (typically up to about 13%) soluble in water to produce a highly acidic liquid, which decomposes violently, liberating heat, chlorine gas and nascent oxygen. When aqueous chlorine dioxide solution is spilled, noxious vapor of chlorine dioxide gas is readily liberated to the atmosphere. Agitation of spilled chlorine dioxide solution can cause increased release of vapors to the atmosphere. Spraying with water can cause such undesirable agitation and, in addition, can cause an unwanted temperature increase in the spilled material, with consequent increased vapor release, due to heat of reaction released during rapid mixing of the spray water with the acidic chlorine dioxide solution. Likewise, certain aqueous foams breakdown too rapidly over chlorine dioxide spills or other non-neutral pH liquids, thereby causing rapid heating and vapor release. More persistent foams, while avoiding such undesirable heating of the spilled non-neutral pH liquid, may merely blanket the spill and, perhaps, even inhibit effective access for treatment and clean up.

In view of the foregoing difficulties, strongly acidic liquids, such as chlorine dioxide solution spills, cannot always be effectively treated with current methods. Agents such as known aqueous film-forming foams tend to be too rapidly broken down upon application to such spills, potentially causing excessive heating and increased vapor release and requiring application of an undesirable number of additional layers to maintain an unbroken foam blanket over the spill. In addition, treatment employing certain known AFFFs is unsatisfactory, as chlorine dioxide has been reported to have violent reactions with materials frequently employed in such formulations, such as sugar, sulfur, fluorine and difluroamine.

As noted above, foam stability can be an important consideration for treating acidic or caustic spills. Heating of the hazardous liquid due to the exothermic neutralization reaction can be high enough to raise the temperature of the spilled liquid sufficiently to cause substantial increase in vapor release and deterioration of the foam blanket. Three factors have been suggested to control foam stability. In the first stage of foam life, water drainage may primarily control foam stability. As water drains from the foam films or lamellae, the films thin quickly to a small thickness. In a subsequent stage of foam decay, the bubbles slowly begin to collapse or coalesce into fewer, but larger bubbles. Gas diffusion and, more importantly, water evaporation from the foam lamellae may be the primary cause of foam collapse during this stage. In a final or near final stage, foam lamellae becomes so thin that even small pertabations, such as vibrations, shocks or sudden pressure or temperature changes can cause the remaining foam columns to collapse catastrophically, resulting in breaks or breaches in the foam blanket.

Accordingly, it is an object of the present invention to provide treatment methods and materials to address the problems set forth above. It is a particular object of the invention to provide methods and materials for treatment of hazardous materials spills, especially non-neutral pH liquids, for example chlorine dioxide solutions and other fuming acids and bases. These and other objects and features of the invention will be readily apparent from the following disclosure and Detailed Description of Certain Preferred Embodiments.

SUMMARY

In accordance with a first aspect, aqueous foamable concentrates are provided, comprising foam-forming agent, foam stabilizing polymer and non-aqueous solvent, i.e., solvent additional to water used in the concentrate, effective to solublize the other ingredients of the aqueous foamable concentrate. The aqueous foamable concentrates disclosed here are pH-tolerant and slow-draining. More specifically, foams formed by foaming the aqueous foamable concentrate with water or other aqueous solution are suitable for deployment over non-neutral pH hazardous liquids, including highly-acidic and highly-caustic liquids. The foams are pH-tolerant in that the foam lamellae, when deployed over such non-neutral pH spills, remain slow-draining. That is, water drains from the foam sufficiently slowly so as to avoid excessive heating of the underlying acidic or caustic spill with consequent rapid breaking-up of the foam blanket.

In accordance with another aspect, methods for treating hazardous material spills are provided, in which pH-tolerant and slow-draining foams prepared from the aqueous foamable concentrates disclosed here are deployed over spills of non-neutral pH liquids. In accordance with a preferred and especially advantageous aspect, the foams are formed with non-neutral pH aqueous solutions. For treatment of an acidic spill, a caustic aqueous solution would be employed to produce the foam from the aqueous foamable concentrate. Similarly, a caustic aqueous solution would be used to produce a correspondingly caustic foam for treatment of an acidic spill. In the specific case of a chlorine dioxide liquid spill, a caustic aqueous solution would be employed with the aqueous foamable concentrates disclosed here to produce a caustic, pH-tolerant, slow-draining foam deployed over the chlorine dioxide liquid spill. Caustic aqueous solution drains from the foam into the underlying chlorine dioxide liquid at a rate sufficiently slow to avoid overheating of the chlorine dioxide liquid and increased vapor release beyond merely containing the chlorine dioxide liquid and vapors. The caustic foam serves to, therefore, neutralize or partially neutralize the chlorine dioxide liquid as it breaks down, and the slow-draining nature of the film preserves the integrity of the foam blanket and its vapor containment performance during the neutralization process. In accordance with especially preferred embodiments, non-neutral pH foams disclosed here, deployed over an oppositely non-neutral pH spill (i.e., caustic foam deployed over a $ClO_2$ or other acidic spill, or acidic foam deployed over a caustic spill) in sufficient quantity (i.e., in sufficient foam density and thickness) to neutralize the spill to pH 7±1, are sufficiently pH-tolerant and slow-draining to remain as a substantially continuous blanket over the spill at least about 15 minutes, more preferably at least about 30 to 60 minutes even when the pH difference between the foam and the original spill is 8 pH units or more, preferably even 12 pH units or more.

It is a particular advantage of the aqueous foamable concentrates according to these preferred embodiments, that they are suitable for mixing with either acidic or caustic aqueous solutions in the foaming process, and the resulting foams are suitable for treating numerous different acidic and caustic liquid spills, including chlorine dioxide liquid spills which are known to be adversely reactive with the components of many known foamable concentrates. Additional aspects and advantages of the present invention will be better understood from the following Detailed Description of Certain Preferred Embodiments.

DETAILED DESCRIPTION OF CERTAIN PREFERRED EMBODIMENTS

As disclosed above, the methods and materials of the present invention are suitable for treatment of a wide range of hazardous material spills, and have special advantage in the treatment of acidic and caustic liquids. For purposes of illustration, but not limitation, preferred embodiments of the invention will be further discussed below with particular reference to treatment of chlorine dioxide spills, such as might be encountered in a paper production facility. It should be noted that all percentages or parts measurements referred to here are intended to mean percent or parts by weight, based on the weight of the fully formulated aqueous foamable concentrate.

Aqueous foamable concentrates disclosed here comprise an aqueous solution of one or more foam forming agents, such as surfactants, a water soluble or miscible non-aqueous solvent and a foam stabilizing polymer. Slow-draining, pH-tolerant, non-neutral pH foam prepared from aqueous foamable concentrates in accordance with certain preferred embodiments provide significant advantage in the treatment of chlorine dioxide spills and other non-neutral pH hazardous materials spills, such as fuming acids and bases. Without wishing to be bound by theory, these non-neutral pH foams are believed to slowly neutralize the spill by the stabilized collapse or breakdown of the foam deployed over the spill, and also effectively to scrub any fumes from the spill which travel through the foam blanket. An additional advantage in the treatment of the hazardous material spill is vapor suppression provided by the substantially continuous foam blanket deployed over the spill. Since the stabilized collapse of the foam does not excessively increase the temperature of the spill by heat released from the neutralization reaction, a more continuous foam blanket is maintained along with consequent reduction in breaches or breaks in the foam blanket through which vapor can escape.

It is a further advantage of the methods and materials disclosed here, that the aqueous foamable concentrates can be foamed using inexpensive non-neutral pH aqueous liquid which may be readily available in the plant or facility in which the spill has occurred. As indicated above, acidic foams, that is, foams formed by mixing the aqueous foamable concentrate with an acidic aqueous liquid are deployed advantageously over caustic spills, whereas caustic foams prepared by mixing the aqueous foamable concentrates with caustic or alkaline aqueous liquid are advantageously deployed over acidic spills, such as chlorine dioxide liquid spills. Caustic aqueous liquid can typically be made readily available for such use in a paper processing plant where chlorine dioxide is employed. Suitable alkaline aqueous liquids for such use include, for example, a 2-3 percent caustic solution.

As indicated above, the aqueous foamable concentrates disclosed here comprise one or more foam-forming agents. In accordance with preferred embodiments, such foam-forming agents are hydrocarbon surfactants, including, for example, sodium alkyl. sulfates in the $C_8$-$C_{16}$ range, sodium alpha olefin sulfonates, and alkylpolyglycosides. In general, as used here, the surfactant which forms the foam is a foamable surfactant when used in combination with the other components of the aqueous foamable concentrate. Suitable hydrocarbon surfactants are commercially available or readily produced for use in aqueous foamable concentrates disclosed here, to produce pH-tolerant slow-draining foams when mixed with water or, more preferably, non-neutral pH aqueous liquid. Exemplary suitable surfactants including APG325S available from Henkel Corporation, Cincinnati, Ohio, Sulfotex 110 available from Henkel Corporation, Cincinnati, Ohio, and Bio-Terge AS-40 available from Stepan Company, Northfield, Ill. In accordance with certain preferred embodiments, aqueous foamable concentrates comprise from about 2 to 12 wt. % sodium decyl sulfate, preferably about 4 to 12 wt. %, most preferably about 8%. In accordance with certain especially preferred embodiments, alkyl polyglycoside is used in an amount of 2 to 14 wt. % together with sodium decyl sulfate, more preferably about 4 to 12 wt. %, most preferably about 8 wt. %. Additional and alternative suitable foam-forming agents will be apparent to those skilled in the art in view of the present disclosure.

The aqueous foamable concentrates disclosed here comprise stabilizer polymer, as stated above. In general, as used here, suitable stabilizer polymers are those which help control the drain and/or collapse rate of the foam when it is deployed over a spill. Preferred stabilizer polymers include those which in composition with the other ingredients of the foamable concentrate, produce a foam with a stability in accordance with the preferred performance characteristics disclosed herein. Suitable foam stabilizer polymers are commercially available or readily produced for use in aqueous foamable concentrates in accordance with preferred embodiments, including many of the biogums or plant gums, for example, xanthan gum and modified guar gums, such as carboxymethyl-2-hydroxypropyl-propyl-ether guar gum and 2-hydroxy-3-(trimethyl ammonium)-propyl-ether-chloride guar gum. Especially preferred for use as the foam stabilizer polymer in aqueous foamable concentrates disclosed here, are xanthan gums, polysaccharide resins having an average molecular weight of about 2 million to 7 million, more preferably about 3 million to 5 million, e.g., about 4 million. Suitable commercially available foam stabilizers include, for example, xanthan gums available from Keltrol Biopolymers, San Diego, Calif., in various grades, for example, as Kelco BT. Xanthan gums having molecular weight less than about 1 million typically yield aqueous foams which tend to be less stable. As foam stabilizer polymer for certain preferred embodiments, xanthan gum is used in an amount from about 0.2 to 2.0 wt. %, more preferably about 0.6 to 1.8 wt. %, most preferably about 1.2 wt. % Other suitable foam stabilizer polymers will be apparent to those skilled in the art given the benefit of the present disclosure.

As indicated above, the aqueous foamable concentrates disclosed here further comprise solvent in addition to the water content of the concentrate. In general, as used here, the solvent will be one that suitably solvates the other components of the aqueous foamable concentrate. To avoid confusion, such additional solvent is sometimes referred to here as non-aqueous solvent, although it may co-solvate at least certain components of the concentrate with the water content thereof. In accordance with preferred embodiments, water soluble or water miscible solvents are selected which act as hydrotropes to keep surfactants in solution and to flatten out the temperature versus viscosity curve for the aqueous foamable concentrate. They also improve foam quality by increasing the foam expansion ratio and slowing down the drain rate of the foam deployed as a blanket over a chlorine dioxide spill or other hazardous liquid. Suitable solvents include, for example, propylene glycol, ethylene glycol, glycerol, diethylene. glycol monobutyl ether (Butyl Carbitol™), dipropylene glycol mono-n-propyl ether, dipropylene glycol monomethyl ether, and hexylene glycol. This solvent is effective, together with the water content of the aqueous foamable concentrate, to solublize the ingredients of the concentrate and render the concentrate foamable. Most preferably, the concentrate is sufficiently solvated to be readily foamable using known equipment and methods. In certain preferred embodiments employing glycol solvent, such solvent may advantageously be used in an amount from about 5 wt. % to 10 wt. %. As further discussed below, these concentrations yield about 0.3 wt. % to about 1.0 wt. % when diluted and foamed, that is, when the aqueous foamable concentrate is foamed with water or, more preferably, non-neutral pH aqueous liquid for deployment over a chlorine dioxide spill or other hazardous material. In other preferred embodiments, the aqueous foamable concentrates employ sodium alpha olefin sulfonate as the foamable surfactant in an amount of from about 4 to 20 wt. %, more preferably about 8 to 16 wt. %, most preferably about 12 to 13 wt. %. In accordance with these preferred embodiments, butyl carbitol is employed as solvent, preferably in an amount from about 2 to 18 wt. %, more preferably about 8 to 12 wt. %, most preferably about 10 wt. %. In accordance with other preferred embodiments, propylene glycol is employed as solvent, preferably in the same weight percentages recited above for butyl carbitol solvent. Numerous additional suitable solvents for the aqueous foamable concentrates disclosed here are commercially available or readily prepared, and will be apparent to those skilled in the art given the benefit of the present disclosure.

Various additional ingredients or components may be included in the aqueous foamable concentrates disclosed here. Optional additional components include, for example, corrosion inhibitors, buffers and anti-microbial or other preservative agents, such as formaldehyde, glutaraldehyde, or a cationic surfactant. Preferably, a bactericide is added as a preservative to prevent decomposition of the aqueous foamable concentrate by bacteria during long-term storage. Long-term storage (e.g., several weeks or more) of the aqueous foamable concentrate may further be improved by inclusion of a biocide to prevent biodegradation, although surfactants in the concentrate typically will suppress biodegradation for a number of weeks. Suitable materials for each such optional or additional ingredient are commercially available or readily prepared, and will be apparent to those skilled in the art in view of the present disclosure.

It will be within the ability of those skilled in the art, given the benefit of the present disclosure, to prepare aqueous foamable concentrates as disclosed using known and conventional methods and equipment. Similarly, it will be within the ability of those skilled in the art, given the benefit of the present disclosure, to use such aqueous foamable concentrates to prepare foam and to deploy such foam over a hazardous material spill, such as chlorine dioxide liquid or other hazardous materials. In that regard, the aqueous foamable concentrates typically are diluted to about 5.5 to 6.5 wt. % in water or non-neutral pH aqueous liquid prior to turbulation to produce a foam. While a typical dilution is approximately 6 wt. %, a substantially wider range will be functional, depending on the specific formulation of a particular aqueous foamable concentrate. In general, it will be within the ability of those skilled in the art to prepare foams having suitable dilution and pH for a particular intended application.

As indicated above, it is an especially advantageous aspect of certain preferred embodiments to foam the aqueous foamable concentrates using non-neutral pH aqueous liquid. As used here, a "non-neutral pH" aqueous liquid or solution has a pH greater than 8.5 or lower than 4.5. Especially preferred is aqueous liquid having a pH greater than 9.5 or lower than 3.5, most preferably lower than 2.5, for example, about 10.0 or higher on the caustic side and about 2.0 or lower on the acidic side. The aqueous foamable concentrates in accordance with highly preferred embodiments are pH-tolerant, being suitable for foaming with either acidic or caustic aqueous liquid to produce foam suitable for treating a caustic or acidic material spill, respectively, such as fuming acid or base, especially chlorine dioxide liquid spills. In this regard, the term "hazardous material" and similar terms are used here in their broadest sense to mean materials which pose a present, imminent or potential hazard to person or property by contact or other exposure. Exemplary uses of the stable, pH-tolerant, non-neutral pH foams prepared from aqueous foamable concentrates in accordance with preferred embodiments include treatment and/or containment of spills or leaks of hazardous liquids from pipelines or containers, such as tanks or vehicles, especially spills or leaks occurring in a building or other confined space. Hazardous materials also can be treated in situ with the foam.

As indicated above, it is especially advantageous to employ acidic aqueous solution to form a foam from the aqueous foamable concentrate, especially acidic aqueous solution having a pH of 2 or less, for treatment of a caustic or alkaline spill. Suitable acidic aqueous solutions will be apparent to those skilled in the art in view of the present disclosure and include, for example, aqueous solutions of organic or mineral acids such as acetic acid, citric acid, oxalic acid, sulfuric acid, or phosphoric acid. Correspondingly, for treatment of acidic spills, caustic aqueous solutions having a pH of 9.5 or greater can be employed to foam the aqueous foamable concentrate. Suitable caustic aqueous solutions will be apparent to those skilled in the art in view of the present disclosure and include, for example, aqueous solutions of alkali metal hydroxides, ammonium hydroxide, amines and alkanolamines. Suitable amines include primary, secondary and tertiary amines in which the alkyl groups have preferably 1-3 carbon atoms, and mono-, di-, and tri-alkanol amines having preferably 2-3 carbon atoms in each alkanol group. As alkali metal hydroxides, sodium or potassium hydroxide are preferred.

From the foregoing disclosure and detailed description of certain preferred embodiments, it will be recognized that the aqueous foamable concentrates disclosed here can produce pH-tolerant, slow-draining foams highly suited to the blanketing and neutralization of non-neutral pH hazardous material spills and, as such, may be referred to as a universal hazardous material treating agent. The aqueous foamable concentrate can be foamed to many times its original volume with water or non-neutral pH aqueous solution, such that storing and using the concentrate can be both convenient and cost-effective. Typically, the aqueous foamable concentrate is mixed with the water or non-neutral pH aqueous solution just prior to use. Preferably, the concentrate is diluted wiwith sufficient water or non-neutral pH aqueous solution to produce a composition desirably containing about 90 to 96 wt. % diluent and about 4 to 10 wt. % aqueous foamable. concentrate. Mixing can be accomplished, for example, by combining the concentrate and aqueous liquid in a circulating system and forcing the mixture at a high linear velocity through a conduit having a small cross-sectional area.

Various aspects of certain preferred embodiments are illustrated in the following examples.

EXAMPLE 1

To 72.8 g of water at 25-30° C. was added 8 g of APG325S and 8 g of Sulfotex 110. With continued agitation, 10 g of butyl carbitol was slurried with 1.2 g of Keltrol BT and added to the mixture to form a pH-tolerant aqueous foamable concentrate. To form pH-tolerant, slow-draining foam solution, 94 parts by volume of caustic aqueous solution, specifically, 3% by weight NaOH, was slowly added to 6 parts by volume of the aqueous foamable concentrate with continuous agitation until homogenous. The foam was then generated from the above solution using a laboratory pneumatic foam generator.

The foam was applied at the rate of 100 ml of solution to a 100 ml spill of 10-12% chlorine dioxide solution having pH of 1.8. The foam was applied as a substantially continuous 2 inch thick blanket over the spill. The pH of the chlorine dioxide spill was measured every 2 minutes over one hour. The pH of the underlying solution was neutralized to a pH of greater than 8 after 14 minutes. The foam blanket remained intact during the neutralization reaction with no substantial breaks or breaches in the foam to permit substantial chlorine dioxide vapor release.

EXAMPLE 2

To 72.8 g of water at 25-30° C. was added 8 g of APG325S and 8 g of Sulfotex 110. With continued agitation, 10 g of propylene glycol was slurried with 1.2 g of Keltrol BT and added to the mixture to form a pH-tolerant aqueous foamable concentrate. To form pH-tolerant, slow-draining foam solution, 94 parts by volume of a 3% by weight NaOH aqueous solution was slowly added to 6 parts by volume of the aqueous foamable concentrate with agitation until homogenous. The foam was generated from the above solution using a laboratory pneumatic foam generator.

The foam was applied at the rate of 100 mls of solution to a 100 ml spill of 10-12% chlorine dioxide solution. The foam was applied as a substantially continuous 2 inch thick blanket over the spill. The pH of the underlying chlorine dioxide spill was measured every 2 minutes over one hour. The pH of the underlying solution was neutralized to a pH of greater than 8 after 12 minutes. The foam blanket remained intact during the neutralization reaction with no substantial breaks or breaches in the foam to permit substantial chlorine dioxide vapor release.

EXAMPLE 3

To 76.3 g of water at 25-30° C. was added 12.5 g of Bio-Terge AS-40. With continued agitation, 10 g of propylene glycol was slurried with 1.2 g of Keltrol BT and added to the mixture to form a pH-tolerant aqueous foamable concentrate. To form pH-tolerant, slow-draining foam solution, 94 parts by volume of a 3% by weight NaOH aqueous solution was slowly added to 6 parts by volume of the aqueous foamable concentrate with agitation. The foam was generated from the above solution using a laboratory pneumatic foam generator.

The foam was applied at the rate of 100 ml to a 100 ml spill of 10-12% chlorine dioxide solution. The foam was applied as a substantially continuous 1 inch thick blanket over the spill. The underlying chlorine dioxide spill was measured every 2 minutes over one hour. The pH of the underlying solution was neutralized to a pH of greater than 8 after 8 minutes. The foam blanket remained intact during the neutralization reaction with no substantial breaks or breaches in the foam to permit substantial chlorine dioxide vapor release.

Variations of the above embodiments are contemplated. For example, other components can be included in the foam concentrate and the foam concentrate can be used for applications other than neutralizing chlorine dioxide spills. The scope of the invention is only limited by the breadth of the appended claims.

We claim:

1. An aqueous foam comprising an aqueous foamable concentrate foamed with non-neutral pH aqueous liquid, the aqueous foamable concentrate comprising a form-forming agent, a foam stabilization polymer, and a non-aqueous solvent.

2. The aqueous foam of claim 1, wherein the non-neutral pH liquid has a pH of less than 4.5 and forms an acidic foam.

3. The aqueous foam of claim 1, wherein the non-neutral pH liquid has a pH of greater than 9.5 and forms a caustic foam.

4. The method of claim 1, wherein the non-neutral pH foam remains as a continuous blanket of substantially constant thickness over the spill for at least about 15 minutes as the liquid drains from the non-neutral pH foam.

5. The method of claim 1, wherein the non-neutral pH foam remains as a continuous blanket of substantially constant thickness over the spill for at least about 30 minutes as the liquid drains from the non-neutral pH foam.

6. The method of claim 1, wherein the non-neutral pH foam remains as a continuous blanket of substantially constant thickness over the spill for at least about 60 minutes as the liquid drains from the non-neutral pH foam.

7. The method of claim 1, wherein the non-neutral pH foam remains as a continuous blanket of substantially constant thickness over the spill for at least about 15 minutes, as the liquid drains from the non-neutral pH foam, when a difference between a pH of the foam and a pH of the spill, prior to deployment of the non-neutral pH foam, is 8 pH units or more.

8. The method of claim 1, wherein the non-neutral pH foam remains as a continuous blanket of substantially constant thickness over the spill for at least about 15 minutes, as the liquid drains from the non-neutral pH foam, when a difference between a pH of the foam and a pH of the spill, prior to deployment of the non-neutral pH foam, is 12 pH units or more.

9. The method of claim 1, wherein the non-neutral pH foam remains as a s continuous blanket of substantially constant thickness over the spill for at least about 30 minutes, as the liquid drains from the non-neutral pH foam, when a difference between a pH of the foam and a pH of the spill, prior to deployment of the non-neutral pH foam, is 8 pH units or more.

10. The method of claim 1, wherein the non-neutral pH foam remains as a continuous blanket of substantially constant thickness over the spill for at least about 30 minutes, as the liquid drains from the non-neutral pH foam, when a difference between a pH of the foam and a pH of the spill, prior to deployment of the non-neutral pH foam, is 12 pH units or more.

11. The method of claim 1, wherein the non-neutral pH foam remains as a continuous blanket of substantially constant thickness over the spill for at least about 60 minutes, as the liquid drains from the non-neutral pH foam, when a difference between a pH of the foam and a pH of the spill, prior to deployment of the non-neutral pH foam, is 8 pH units or more.

12. The method of claim 1, wherein the non-neutral pH foam remains as a continuous blanket of substantially constant thickness over the spill for at least about 60 minutes, as the liquid drains from the non-neutral pH foam, when a difference between a pH of the foam and a pH of the spill, prior to deployment of the non-neutral pH foam, is 12 pH units or more.

13. The method of claim 1, wherein the non-neutral pH aqueous liquid drains from the non-neutral pH foam sufficiently slowly so as to avoid excessive heating of the spill due to at least one of heat of solution and heat of neutralization.

14. The method of claim 1, wherein the non-neutral pH foam scrubs, in-situ, non-neutral fumes as the fumes are released from the spill and pass through the blanket of foam.

15. The method of claim 14, wherein the scrubbing substantially neutralizes the fumes to a pH of between 6 and 8.

16. The method of claim 1, wherein the pH of the non-neutral pH aqueous solution is controlled to be at least 8.5 and to form a caustic foam that is deployed over acidic spills.

17. The method of claim 1, wherein the pH of the non-neutral pH aqueous solution is controlled to be no more than 3.5 and to form an acidic foam that is deployed over caustic spills.

18. The method of claim 1, wherein the pH of the non-neutral pH aqueous solution is controlled to be one of at least 10 and no more than 2.0.

19. The method of claim 1, further comprising adding a caustic agent, independent of and separate from the foamable concentrate, to a liquid to raise a pH of the liquid to form the non-neutral pH aqueous liquid for use on an acidic spill.

20. The method of claim 19, wherein the caustic agent is added to the liquid before or after the foamable concentrate is added to the liquid.

21. The method of claim 19, wherein the caustic agent is added in an amount of at least 3% by weight to the liquid to raise the pH of the liquid.

22. The method of claim 1, further comprising adding an acidic agent, independent of and separate from the foamable concentrate, to a liquid to lower a pH of the liquid to form the non-neutral pH aqueous liquid for use on a caustic spill.

23. The method of claim 22, wherein the acidic agent is added to the liquid before or after the foamable concentrate is added to the liquid.

24. The method of claim 22, wherein the acidic agent is added in an amount of at least 3% by weight to the liquid to lower the pH of the liquid.

25. The method of claim 1, wherein the foam contains at least 90% by volume non-neutral pH aqueous solution and no more than 20% by volume foamable concentrate.

26. The method of claim 1, wherein the foam contains no more than 96% by volume non-neutral pH aqueous solution and at least 4% by volume foamable concentrate.

* * * * *

UNITED STATES PATENT AND TRADEMARK OFFICE

CERTIFICATE OF CORRECTION

PATENT NO. : 7,381,696 B2
APPLICATION NO. : 10/074814
DATED : June 3, 2008
INVENTOR(S) : Hubert et al.

It is certified that error appears in the above-identified patent and that said Letters Patent is hereby corrected as shown below:

Col. 8, replace claim 1, (incorrect claim) with the following claim:
1. A method for treating a non-neutral pH hazardous material spill comprising:
producing a slow draining non-neutral pH foam by foaming an aqueous foamable concentrate with non-neutral pH aqueous liquid, the concentrate being tolerant to the non-neutral pH of the aqueous liquid in that the non-neutral pH aqueous liquid continues to drain slowly during treatment from the non-neutral pH foam after being deployed over a non-neutral pH hazardous material spill;
controlling a pH of the non-neutral pH aqueous liquid to be opposite to a pH of the non-neutral pH hazardous material spill; and
deploying the non-neutral pH foam over the non-neutral pH hazardous material.

Col. 8, replace claim 2, (incorrect claim) with the following claim:
2. The method of claim 1, wherein the pH of the non-neutral pH liquid is controlled to be less than 4.5 and form an acidic foam that is deployed over caustic spills.

Col. 8, replace claim 3, (incorrect claim) with the following claim:
3. The method of claim 1, wherein the pH of the non-neutral pH liquid is controlled to be greater than 9.5 and form a caustic foam that is deployed over acidic spills.

In claim 9, column 9, line 6 delete “as a s continuous”, and insert --as a continuous-- in place thereof.

In claim 25, column 9, line 38, delete “no more than 20% by volume”, and insert --no more than 10% by volume-- in place thereof.

Signed and Sealed this

Seventeenth Day of February, 2009

JOHN DOLL
*Acting Director of the United States Patent and Trademark Office*

UNITED STATES PATENT AND TRADEMARK OFFICE

CERTIFICATE OF CORRECTION

PATENT NO. : 7,381,696 B2

APPLICATION NO. : 10/074814

DATED : June 3, 2008

INVENTOR(S) : Hubert et al.

It is certified that error appears in the above-identified patent and that said Letters Patent is hereby corrected as shown below:

Col. 8, replace claim 1, lines 36-40, (incorrect claim) with the following claim:
1. A method for treating a non-neutral pH hazardous material spill comprising:
producing a slow draining non-neutral pH foam by foaming an aqueous foamable concentrate with non-neutral pH aqueous liquid, the concentrate being tolerant to the non-neutral pH of the aqueous liquid in that the non-neutral pH aqueous liquid continues to drain slowly during treatment from the non-neutral pH foam after being deployed over a non-neutral pH hazardous material spill;
controlling a pH of the non-neutral pH aqueous liquid to be opposite to a pH of the non-neutral pH hazardous material spill; and
deploying the non-neutral pH foam over the non-neutral pH hazardous material.

Col. 8, replace claim 2, lines 41 and 42, (incorrect claim) with the following claim:
2. The method of claim 1, wherein the pH of the non-neutral pH liquid is controlled to be less than 4.5 and form an acidic foam that is deployed over caustic spills.

Col. 8, replace claim 3, lines 43-45, (incorrect claim) with the following claim:
3. The method of claim 1, wherein the pH of the non-neutral pH liquid is controlled to be greater than 9.5 and form a caustic foam that is deployed over acidic spills.

In claim 9, column 9, line 6 delete “as a s continuous”, and insert --as a continuous-- in place thereof.

UNITED STATES PATENT AND TRADEMARK OFFICE

CERTIFICATE OF CORRECTION

PATENT NO. : 7,381,696 B2
APPLICATION NO. : 10/074814
DATED : June 3, 2008
INVENTOR(S) : Hubert et al.

It is certified that error appears in the above-identified patent and that said Letters Patent is hereby corrected as shown below:

In claim 25, column 9, line 38, delete "no more than 20% by volume", and insert --no more than 10% by volume-- in place thereof.

This certificate supersedes the Certificate of Correction issued February 17, 2009.

Signed and Sealed this

Seventeenth Day of March, 2009

JOHN DOLL
*Acting Director of the United States Patent and Trademark Office*